(12) United States Patent
Kaikkonen et al.

(10) Patent No.: US 6,533,454 B1
(45) Date of Patent: *Mar. 18, 2003

(54) SURGICAL SYSTEM FOR TISSUE FIXATION

(75) Inventors: Auvo Kaikkonen, Tampere (FI); Piet E. Haers, Guildford (GB); Hermann Sailer, Zurich (CH); Harri Happonen, Tampere (FI); Riitta Suuronen, Espoo (FI); Timo Waris, Helsinki (FI); Olli Karhi, Oulu (CH); Pertti Törmälä, Tampere (FI)

(73) Assignee: Bionx Implants Oy, Tampere (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/410,288

(22) Filed: Sep. 30, 1999

(51) Int. Cl.[7] .................................................. A61B 6/08
(52) U.S. Cl. .......................................... 378/205; 378/63
(58) Field of Search ................................. 378/207, 206, 378/205, 162, 63

(56) References Cited

U.S. PATENT DOCUMENTS

| | | | | |
|---|---|---|---|---|
| 4,836,671 A | * | 6/1989 | Bautista ........................ 356/1 |
| 5,059,206 A | | 10/1991 | Winters | |
| 5,261,914 A | * | 11/1993 | Warren ......................... 606/73 |
| 5,290,281 A | * | 3/1994 | Tschakaloff .................. 606/28 |
| 5,522,843 A | * | 6/1996 | Zang ........................... 606/232 |
| 5,539,798 A | * | 7/1996 | Asahina et al. ............ 378/98.5 |
| 5,569,250 A | * | 10/1996 | Sarver et al. ................. 606/69 |
| 5,735,854 A | * | 4/1998 | Caron et al. .................. 606/73 |
| 5,779,706 A | | 7/1998 | Tschakaloff | |
| 5,923,727 A | * | 7/1999 | Navab ......................... 378/207 |
| 6,010,513 A | * | 1/2000 | Tormala et al. ............. 606/142 |
| 6,118,845 A | * | 9/2000 | Simon et al. ................. 378/62 |

FOREIGN PATENT DOCUMENTS

| | | |
|---|---|---|
| DE | 29513342 U | 11/1995 |
| EP | 0867149 A | 9/1998 |
| NL | 9201974 | 1/1994 |
| WO | 95/06439 A | 3/1995 |
| WO | 99/26544 | 6/1999 |
| WO | 99/44529 | 9/1999 |

* cited by examiner

*Primary Examiner*—David O. Reip
(74) *Attorney, Agent, or Firm*—Kenyon & Kenyon

(57) ABSTRACT

A surgical tissue fixation system is described, including: (1) a bioabsorbable tissue fixation plate having optionally a plurality of through-holes arranged in alternating relation along the plate; (2) bioabsorbable fasteners adapted for insertion into the through-holes to secure the plate to underlying bodily tissue or bone; and (3) an installation instrument which triggers (strikes or shoots) fasteners one after one, in rapid succession, into the through-holes made through the plate and into the underlying bodily tissue or bone, which also optionally includes drillholes.

13 Claims, 5 Drawing Sheets

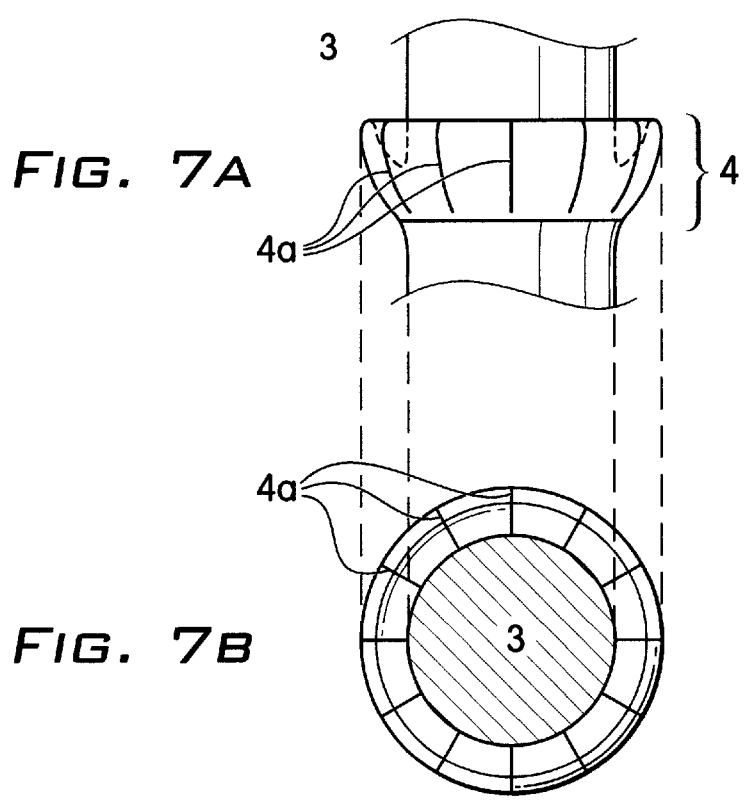
FIG. 7A
FIG. 7B
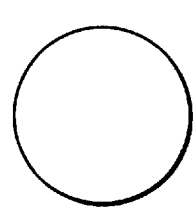
FIG. 8A
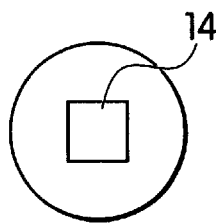
FIG. 8B
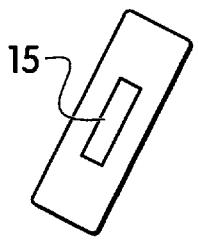
FIG. 8C
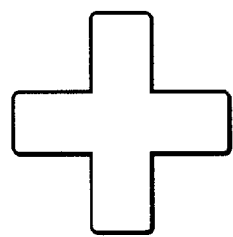
FIG. 8D
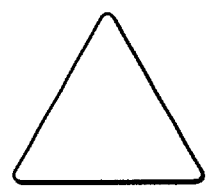
FIG. 8E

SURGICAL SYSTEM FOR TISSUE FIXATION

FIELD OF THE INVENTION

The present invention relates generally to surgical tissue fixation equipment and systems and, more particularly, to bioabsorbable fixation systems including bodily tissue fixation hardware comprising biocompatible, bioabsorbable (resorbable) polymeric or composite plates and fasteners for securing the plates to bodily tissue for fixation thereof, and an installation instrument which triggers (strikes) fasteners one after one into through-bores (holes) made through the plate and into the underlying bodily tissue.

BACKGROUND OF THE INVENTION

Traditional orthopedic and traumatological and craniomaxillo-facial fixation systems to facilitate bone fracture healing (osteosynthesis) or soft tissue-to-bone healing typically employ metallic hardware, e.g., plates, screws, rods and the like, formed of biocompatible, corrosion resistant metals such as titanium and stainless steel. Typical metallic plates are described, e.g., in the book F. Séquin and R. Texhammar, AO/ASIF Instrumentation, Springer-Verlag, Berlin, Heidelberg, 1981, p. 21-22, 55-79, 107-108, 117-122, the entire disclosure of which is incorporated herein by way of this reference. While such systems are generally effective for their intended purposes, they possess a number of inherent shortcomings. For example, metal release to the surrounding tissues (see, e.g., L.-E. Moberg et al. Int. J. Oral. Maxillofac. Surg. 18 (1989) p. 311-314, the entire disclosure of which is incorporated herein by reference) has been reported. Other reported shortcomings are stress shielding (e.g., P. Paavolainen et al., Clin Orthop. Rel. Res. 136 (1978) 287-293, the entire disclosure of which is incorporated herein by reference) and growth restriction in young individuals (e.g., K. Lin et al., Plast. Reconstr. Surg. 87 (1991) 229-235, the entire disclosure of which is incorporated herein by reference). In infants and young children there is the risk that metallic plates and screws sink, as a consequence of skull bone growth, into and below the cranial bone threatening brain (J. Fearon et al., Plast. Reconstr. Surg. 4 (1995) 634-637, the entire disclosure of which is incorporated herein by reference). Therefore, it is recommended generally that non-functional implants should be removed, at least in growing individuals (see, e.g., C. Lindqvist, Brit. J. Oral Maxillofac. Surg. 33 (1995) p. 69-70, the entire disclosure of which is incorporated herein by reference).

Especially in maxillofacial and in cranial surgery metallic mini plates are popular (see, e.g., W. Muhlbauer et al., Clin. Plast. Surg. 14 (1987) 101-111; A. Sadove and B. Eppleg, Ann. Plast. Surg. 27 (1991) 36-43; R. Suuronen, Biodegradable Self-reinforced Polylactide Plates and Screws in the Fixation of Osteotomies in the Mandible, Doctoral Thesis, Helsinki University, Helsinki, 1992, p. 16, the entire disclosures of which are incorporated herein by reference; and see the references cited in the previous references). Mini plates are small, thin, narrow plates, which have holes for screw fixation. They are located typically on bone perpendicularly over the fracture to fix the bone mass on both sides of the fracture to each others. Typical geometries of mini plates are described, e.g., in U.S. Pat. No. 5,290,281, in FIGS. 6A-6F, the entire disclosure of which is incorporated herein by reference.

The main advantage of metallic plates, screws, etc. (like titanium, stainless steel and cobalt chrome molybdenum plates or screws), is that they are strong, and tough. Ductile metal plates can be deformed or shaped (bent) at room temperature in an operation room by hand or with special instruments to the shape of a form that corresponds to the surface topography of the bone to be fixed, so that the plate can be fixed flush on the bone surface to which the plate is applied.

Because of the shortcomings of metallic plates, bioabsorbable plates have been developed for fracture fixation. Longitudinal, six-hole plates were developed by Eitenmüller et al. for orthopaedic animal studies (European Congress on Biomaterials, Abstracts, Instituto Rizzoli, Bologna, 1986, p. 94, the entire disclosure of which is incorporated herein by reference). However, because of inadequate strength, some of the plates were broken in animal experiments involving fracture fixation.

A particular advantage of bioabsorbable plates is that they can be provided with openings for the insertion of surgical fasteners (like screws) therethrough, while also allowing means to permit the formation of additional fastener openings therethrough during a surgical procedure at the surgeon's discretion, as has been described in European Patent specification EP 0 449 867 B1, the entire disclosure of which is incorporated herein by reference.

However, the main disadvantage of most prior art bioabsorbable plates is that they can be deformed (bent) permanently and safely only at elevated temperatures above the glass transition temperature ($T_g$) of the bioabsorbable polymer, as has been described, e.g., in EP 0 449 867 B1, U.S. Pat. No. 5,569,250 and U.S. Pat. No. 5,607,427, the entire disclosures of which are incorporated herein by reference. Below the respective glass transition temperatures of the bioabsorbable polymers from which they are made, most prior art bioabsorbable plates are brittle and break easily when deformed. Only at temperatures above the $T_g$ of the bioabsorbable polymer from which a given plate is made does the molecular structure of most prior art plates have enough mobility to allow shaping and bending of the plate, without the risk of breaking.

Because the thermal conductivity of most polymeric materials is generally poor, both heating and cooling of bioabsorbable plates are slow processes. Therefore, the clinical use of such prior art plates is tedious, slow and complex, especially if the surgeon must shape the plate several times to make it fit exactly to the form of the bone to be fixed.

K. Bessho et al., J. Oral. Maxillofac. Surg. 55 (1997) 941-945, the entire disclosure of which is incorporated herein by reference, describe a bioabsorbable poly-L-lactide miniplate and screw system for osteosynthesis in oral and maxillofacial surgery. The plates of that reference also must be heated by immersion in a hot sterilized physiologic salt solution, or by the application of hot air, until they become plastic, and only then can those plates be fitted to the surface of the bone being repaired.

EP 0 449 867 B1, the entire disclosure of which is incorporated herein by reference, describes a plate for fixation of a bone fracture, osteotomy, arthrodesis, etc., said plate being intended to be fixed on bone with at least one fixation device, like a screw, rod, clamp or some other corresponding device. The plates of that reference comprise at least two essentially superimposed plates, so as to provide a multilayer plate construction, so that the individual plates of said multilayer plate construction are flexible to provide a change of form of said multilayer plate construction to substantially assume the shape of the bone surface under the operation conditions. That change of form is accomplished by means of an external force, such as by hand and/or by a bending instrument directed to said multilayer plate construction, whereby each individual plate assumes the position of its own with respect to other individual plates by differential motion along the surfaces of the coinciding plates.

Although the above multilayer plate can fit the curved bone surface without heating of the individual plates, the clinical use of such multilayer plates is tedious, because the single plates easily slip in relation to each other before fixation. Additionally the thickness of multilayer plate system easily becomes too thick for cranio maxillofacial applications, causing cosmetic disturbance and increased risks of foreign body reaction.

To avoid the above mentioned shortcomings in the prior art devices, U.S. Pat. Appl. Ser. No. 09/036,259, the entire disclosure of which is incorporated herein by reference, describes strong and tough, uni- and/or biaxially oriented and/or self-reinforced bioabsorbable plates, which are deformable at room temperature, like in operation room conditions, prior to implantation in a patient. The plates described in that application retain their deformed (bent or shaped) form so well at body temperature in tissue conditions (e.g., when implanted on a patient's bone) that they keep the fixed bone fragments in the desired position to facilitate bone fracture healing. When using such plates surgically, the surgeon can bend (and rebend) the plate easily in operation conditions, without needing the slow and tedious heating-bending-cooling procedure of the prior art plates.

While the clinical use of the bioabsorbable plates described in U.S. Pat. Appl. Ser. No. 09/036,259 significantly reduces operation time in comparison to the clinical use of other prior art bioabsorbable plates, the fixation of plates on tissue or bone is still a slow and tedious process. Prior art fixation techniques mainly use screws or screw-type fasteners for plate fixation. However, turning of screws or screw-type fasteners into drill holes is a slow process. For example, in a single maxillo-cranio-facial operation, tens of screws may be used for plate fixation and such an operation may demand hours to complete. On the other hand, manual use of other types of fasteners, like expansion bolts (pins), or plugs or rivets is also a slow and risky process. For example, manual hammering of fasteners, like those described in U.S. Pat. No. 5,261,914 or U.S. Pat. No. 5,607,427, the entire disclosures of which are incorporated herein by reference, can easily be done too strongly, so that the head of the fastener and/or plate and/or underlying tissue(s) is (are) damaged.

Two-component fasteners, like expansion bolts or plugs (such as those described in H. Pihlajamäki et al. ,: A biodegradable expansion plug for the fixation of fractures of the medial malleolus, Ann Chir Gyn 83: 47-52, 1994, the entire disclosure of which is incorporated herein by reference) or pop rivet-type fasteners can be complicated and risky to use because strong expansion of a part of such a fastener can cause extensive compression to the surrounding bone, leading to bone necrosis.

A need, therefore, still exists for a surgical tissue fixation system comprising (a) a bioabsorbable (bioresorbable or biodegradable) plate, which is strong, tough and thin, substantially rigid and deformable (either at room temperature or at an elevated temperature); (b) a bioabsorbable fastener adapted for insertion into through-bores (drill holes) in the bioabsorbable plate, to secure the plate to underlying bodily tissue in a rapid and safe manner; and (c) an installation instrument which installs (e.g., by triggering or striking) the fasteners one after another rapidly, securely and with a minimal trauma into the through-bores made through the plate and into the underlying bodily tissue.

A need also exists for a surgical tissue fixation system comprising a bioabsorbable plate, bioabsorbable fasteners and an installation instrument, which triggers the fasteners one after another into the drill holes made through the plate and optionally also into the underlying bodily tissue, with a single strike or with several consecutive strikes, without the need of turning the fastener around its long axis during installation.

A need also exists for a surgical tissue fixation system comprising a bioabsorbable plate, bioabsorbable fasteners and an installation instrument, which triggers the fasteners one after another precisely into the drill holes in plates, so that the lower surface of the fastener head mates exactly with the upper surface of the plate (or with the countersink surface in the upper part of the drill hole in the plate).

A need also exists for a curved cannula for attaching to the above fixation instrument, to allow application of the fasteners onto bone in areas, e.g., such as the posterior mandible or subcutaneous spaces, where there is no access with straight upright instrumentation.

SUMMARY OF THE INVENTION

In accordance with the present invention, there is provided a surgical tissue fixation system, including a bioabsorbable plate and a bioabsorbable fastener to secure the plate to underlying bodily tissue and an installation tool which triggers the fasteners one after another through drill holes made through the plate and into the underlying bodily tissue. The plate and fastener equipment is particularly adapted for fixating fractured or severed bones, or for affixing a ligament, tendon or connective tissue on a bone or into a drillhole in a bone, to promote rapid and beneficial healing of the treated bones and/or tissues.

In a preferred embodiment of the invention, the installation instrument cooperates as part of a surgical system with one or more specially configured plates, fabricated from bioabsorbable polymeric or composite material, wherein the plates can be secured by a surgeon via a plurality of fasteners to a bone, cartilage, tendon, connective tissue or other bodily tissue being repaired. Other details, objects and advantages of the present invention will become apparent from the following description of the presently preferred embodiments and presently preferred methods of practicing the invention.

BRIEF DESCRIPTION OF THE DRAWINGS

The invention will become more readily apparent from the following description of preferred embodiments, which are shown, by way of example only, in the accompanying drawings.

FIG. 7 shows a surface of a fastener body with a ridge, which has been cut with longitudinal grooves, including a side view (A) and an upper view (B) of the stem and ridge.

FIG. 8 shows typical geometries of the head of the fastener when seen from the upper side of the fastener in the direction of the longitudinal axis of the fastener.

DETAILED DESCRIPTION OF THE INVENTION

According to the invention, the fastener(s) and plate(s) are manufactured of bioabsorbable polymer, polymer alloy or composite material, which is strong and tough and retains its strength in vivo several weeks or months.

Figure 1:
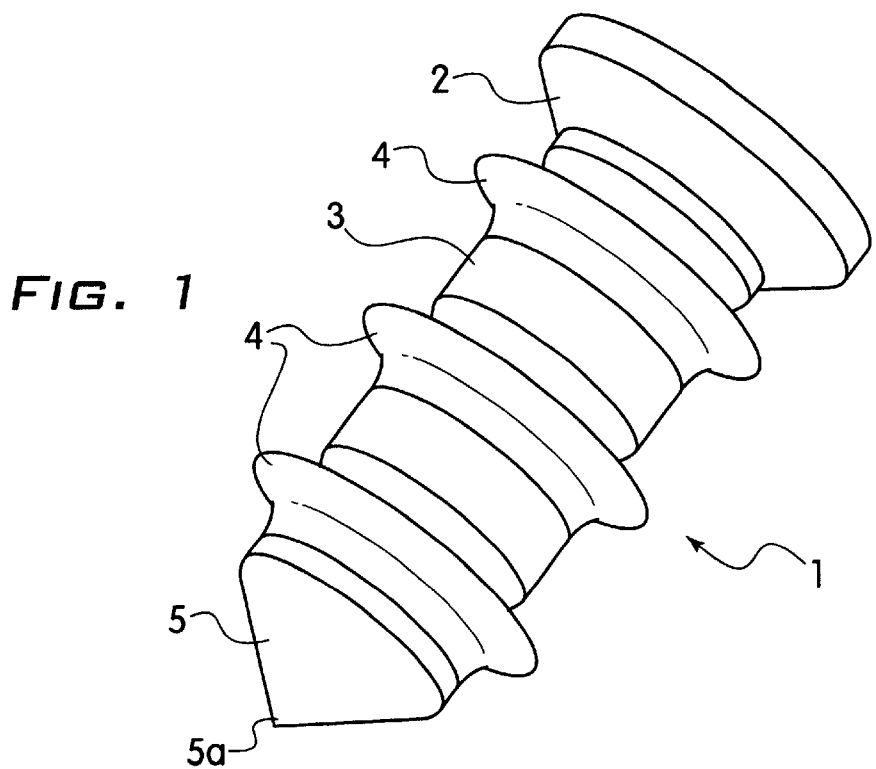
FIG. 1 is a schematic representation of a typical fastener according to the present invention, for securing a bodily tissue fixation plate to underlying bodily tissue, as seen as perspective figures from different directions.

FIG. 1 shows a typical fastener (1) according the invention comprising a proximal head (2), a stem (3), from which one or more protuberances (4) emerge. Typical protuberances are ridges, reaching at least partially around the stem (3), threads, pyramid-like or half ballshaped papillae, barbs, scales, etc. The geometry of protuberances (4) is such, that it allows easy gliding of the fastener into the drill hole in the plate (6 in FIG. 2) and into the bone (7 in FIG. 2) or into an optional drillhole in the bone (10 in FIG. 3), while still locking the fastener effectively into its place, preventing its movements backwards after installation. Finally, according to FIG. 1 the fastener comprises the distal tip (5), which can be conical with a sharp or blunt or rounded end (5a) to facilitate its installation into the drillhole in the plate (and optionally into the drillhole in bone).

According to the invention, the presently preferred bioabsorbable polymeric or composite materials forming the fixation plates (the compositions of which will be later described in greater detail) can be bent and shaped, in operation room conditions or at an elevated temperature, typically at temperatures ranging from about 15° C to 120° C.

A number of geometries are useful for the plate, such as those described in U.S. Pat. Appl. Ser. No. 09/036,259. The plate of the invention is desirably of a thickness of less than about 2 mm and may include a plurality of spaced apart through-bores adapted to accommodate fasteners. Fasteners also can be formed from any suitable biocompatible and bioabsorbable polymeric or composite material from the classes used for forming the plates or from other acceptable materials of similar properties and characteristics. Such materials have been described extensively in prior art, e.g. in U.S. Pat. Appl. Ser. No. 09/036,259.

Figure 2:
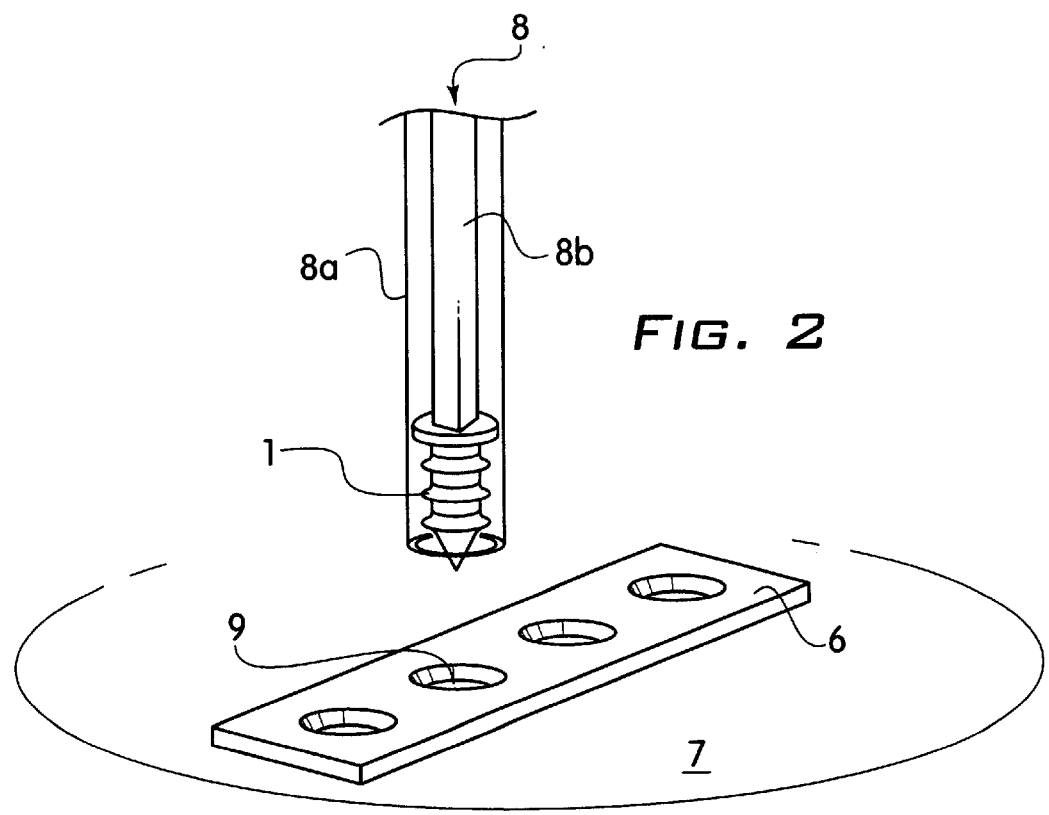
FIG. 2 is a perspective view illustrating a bioabsorbable fixation (osteosynthesis) plate in combination with a fixation fastener, positioned in a relatively elevated position inside of an installation cannula of an installation instrument, for insertion of the fastener within a fastener opening of a fixation plate.

FIG. 2 is a perspective view illustrating a fastener (1) according to the present invention used for fastening of the plate (6) to underlying bodily tissue, like bone (7) during a surgical operation. As suggested herein above, fastener (1) may be formed of any suitable bioabsorbable and biocompatible polymeric or composite material; however, the material must be chosen from those materials having sufficient strength and toughness and hardness whereby the fastener head (2), stem (3) and fastener protuberances (4) and tip (5) (see FIG. 1) do not fail upon the application of pressure to the fastener head (2), which occurs when fastening the bodily tissue fixation plate (6) to underlying bodily tissue (7). Such pressure is applied by triggering the fastener (1) with the installation instrument (8), whose cannula (8a) and piston or tool (8b) are seen in FIG. 2, into a through-bore (9) in the plate and into an optional drillhole (10 in FIG. 3) in tissue (7) under the plate. In the perspective of FIG. 2, a fastener (1) is positioned in a relatively elevated position inside of an installation cannula (8a) (the cross-section of the cannula shows the fastener (1) inside of the cannula) of an installation instrument (8) (not seen totally in this Figure). The fastener (1) can be triggered (shot) into a drillhole (bore) (9) in the plate (6) by pushing it rapidly with the piston (8b) into the drillhole (9).

Figure 3:
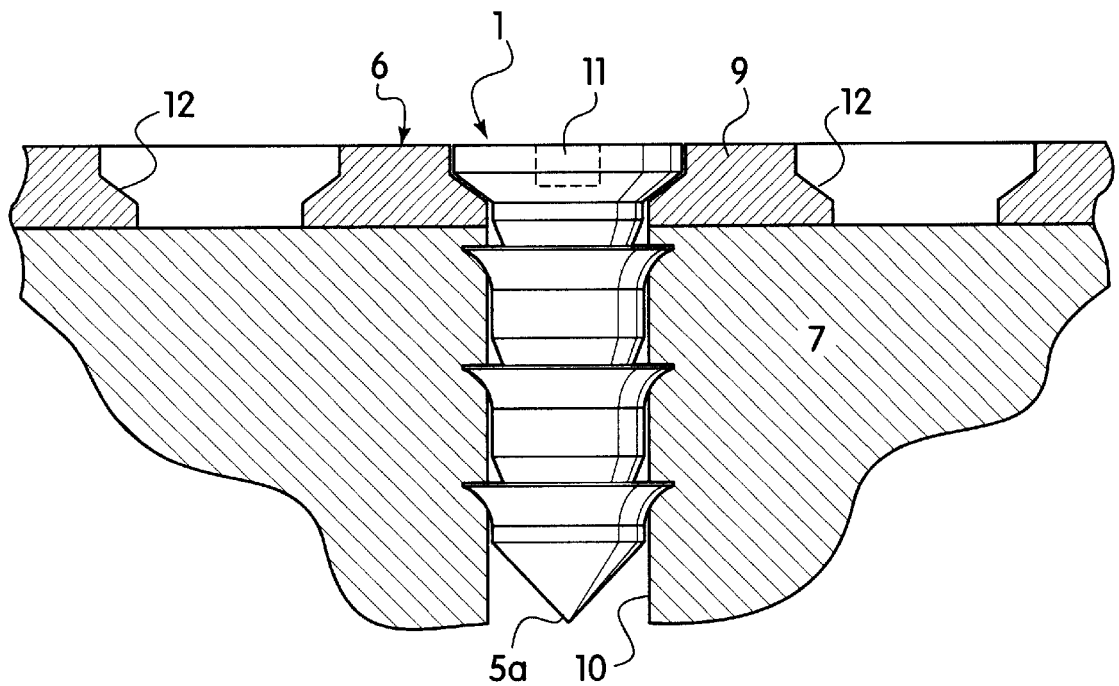
FIG. 3 is a schematic cross-sectional representation of a fixation system (a plate +fastener) according to the present invention, a fastener being applied into a drillhole in a plate and into a drillhole in the underlying bone tissue.

FIG. 3 shows a cross-sectional view of a fastener (1) after having been triggered into a drillhole (9) in the plate (6) and further into a drillhole (10) in the bone (7). The head (2) of fastener (1) may optionally contain a tool receiving notch or recess (11), which may be cylindrical or angular of its cross-section. The notch or recess (11) is configured for receiving the tip of the piston (tool) (8b) and for securing the grip of the tip of the tool inside of the notch or recess with a frictional grip. It is also possible, that the head of fastener (1) is smooth and there is no frictional grip between the head (2) and the tip of the piston (8b). While the tool-receiving portion of fastener head may assume any conventional socket configuration, it is preferred that the head includes a socket shape adapted to minimize the likelihood of inadvertent slippage of the tip of the triggering tool during fastener installation. Moreover, the underside of the fastener head (2) is desirably contoured as conical to mate (conform) to the shape of a fastener head seat (12 in FIG. 3) formed at the upper ends of through-bores (9) of plate (6), thus minimizing the height of the fastener plate profile. It is preferred that the distal end (5) of the stem (3) portion (with protuberances (4) ) of the fastener (1) be formed into a generally pointed configuration (5a), as illustrated, so as to facilitate guidance and insertion of the fastener into both its corresponding through-bore (9) and the preformed receiving hole (10) that may be provided in the underlying bodily tissue (7) being repaired.

The maximum outer diameter D, between the protuberances (see FIG. 5) of the fastener (1) of the present invention is desirably less than about 3.0 mm. Indeed, according to presently preferred embodiments of the invention, the outer diameter is typically approximately 2.0 mm or less for normal service requirements in surgery and up to about 2.5 mm for emergency requirements, and the corresponding nominal bore diameter of throughbores (9 and 10) is preferably about 1.8-1.9 mm or less. Because of the very small diameters of the fasteners (1), they are particularly well-suited for fixation of small and/or non-weight bearing bones or other bodily tissues.

Figure 6A:
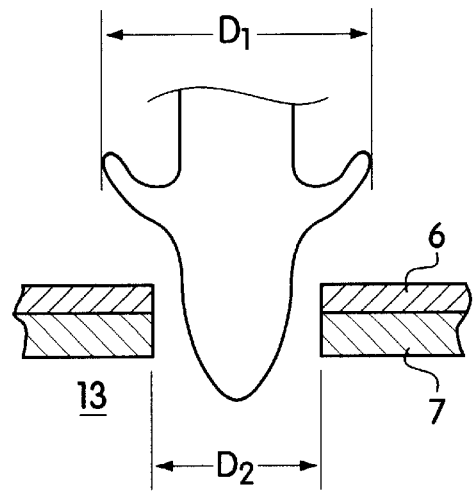
FIG. 6 shows schematically, in a cross-section, elastic bending of a ridge of a fastener during insertion into a drill hole.
Figure 5A:
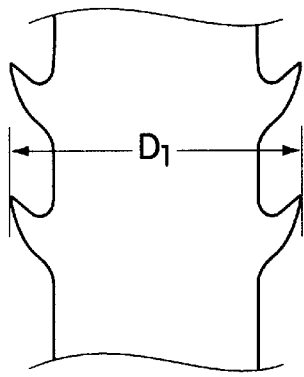
FIG. 5 shows cross-sections of fasteners of the invention, showing different protuberance geometries.
Figure 6B:
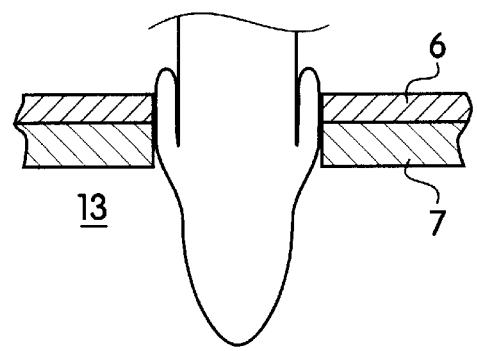
Figure 5B:
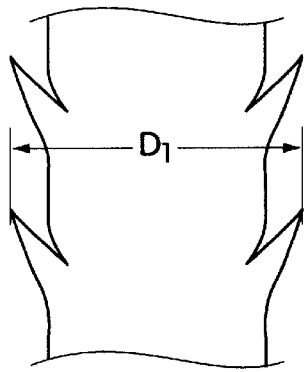
Figure 6C:
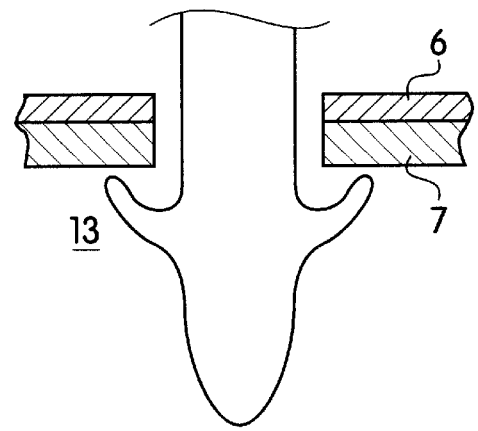

According to an advantageous embodiment of the invention, the protuberances (e.g., scales, ridges or threads) on the fastener have such a structure that they can deform at least partially elastically during insertion of the fastener. FIG. 5 shows schematically in a crosssection such protuberances, (like horizontal ridges), which can deform (bend) elastically during insertion. As shown in FIG. 6, when the maximum outer diameter ($D_1$) of the fastener ($D_1$ = the maximum distance between protuberances on opposite sides of the fastener) is bigger than the diameter ($D_2$) of the drillhole in the plate (6) and in the compact bone (7) below (see FIG. 6A), the protuberances can bend temporarily inside the drillhole in the plate and in the compact bone below the plate (see FIG. 6B), but widen again to almost their original width when they have slipped into the soft tissue or void space (13) below the compact bone. In such a case, the fixation of the fastener is especially strong because the widened protuberances effectively prevent the slippage of the fastener back from the drillhole.

According to FIGS. 7A and 7B, the protuberance (ridge) (4) on the surface of the fastener stem (3) of the invention, has been split to several parts having longitudinal grooves (4a). Such separate ridge parts bend elastically more easily than an intact ridge on insertion of the fastener.

The head of the fastener of the invention also can have different geometries. FIGS. 8A-E show different types of fastener heads, as seen from above. FIG. 8A shows a rounded head. FIG. 8B shows such a head equipped with a quadrangular tool-receiving notch (14). FIG. 8C shows a flat head with a groove-like notch (15). FIG. 8D shows a cross-like head and 8E a triangular head. It is evident that the form of the head of the fastener is not limited to those forms expressly described here.

According to an advantageous embodiment, the fastener of the invention can be cannulated, which means that inside of the fastener there is a longitudinal hole which traverses the fastener. Such a cannulated fastener can be pushed along a metallic guide-wire into the tissue. The guide-wire can facilitate the installation operation in certain cases, e.g. guide-wire(s) can be used to keep the plate and/or damaged tissue in a proper place before the installation of the fastener.

The installation instrument of this invention can be any instrument which triggers (strikes or shoots) the fastener through a cannula by means of a piston through the drillhole in a plate into the underlying bodily tissue. Such instruments have been described, e.g., in U.S. Pat. Appl. Ser. No. 08/887,130 and U.S. Pat. No. 6,010,513, the entire disclosures of which are incorporated herein by reference. Accordingly, the installation instrument has a conduit, such as a cannula, that may be easily inserted into the patient and through which the fastener is delivered to the patient. This conduit is aligned with a seat for holding a fastener and a means for pushing a fastener, such as a piston, so that the pushing means is capable of pushing fastener from its seat, through the conduit and into the patient. In a preferred embodiment of the invention, the shape of the conduit relatively exactly matches the shape of the cross-section of the fastener so that the surgeon may more accurately direct the angle and location at which the fastener enters the patient. In another preferred embodiment, the pushing means may be made to slowly push the fastener from its seat and through the conduit until the distal end of the fastener contacts the drill hole of the plate at the end of the conduit. At that time, the pushing means may be made to accelerate rapidly, thereby inserting the fastener into the drill hole of the plate and into the tissue being treated. An advantage of this embodiment is that the fastener is less likely to become jammed in the conduit while being pushed slowly through it. Further, the conduit, piston, and fastener are subject to less wear, which helps to ensure proper functioning of the instrument during an operation.

The seat for holding fasteners is capable of holding a magazine containing one or more fasteners. When inserted into the seat, the magazine may be positioned so that a fastener is aligned with the pushing means and the conduit leading to the patient. Once a fastener has been inserted into the patient, the magazine may be manually positioned so that another fastener is shifted into position to be inserted. In one embodiment of this invention, the magazine may have means, such as a spring, for automatically moving a fastener into position for insertion once a first fastener has been inserted.

The magazine may be easily removed from the seat during an operation, so that it may be replaced with a magazine containing one or more fasteners, without requiring the conduit to be removed from the patient. Alternatively, the same magazine could be removed, refilled with one or more additional fasteners, and reinserted into the seat, without requiring the removal of the conduit from the patient. In yet another embodiment of the invention, when the magazine is positioned to allow the insertion of one fastener into the patient, a portion of the magazine is accessible to allow the insertion of one or more additional fasteners into the magazine. In this fashion, additional fasteners may be added to the magazine without requiring its removal from the device or the removal of the conduit of the device from the patient.

In a preferred embodiment of the invention, the conduit or cannula of the instrument is easily removable from the rest of the device. This allows the same instrument to be used during an operation with differently shaped conduits, depending upon the location and condition of the plate being fixed and tissue being treated. Thus, for instance, during the same operation, the surgeon could insert fasteners through a straight conduit (cannula), then easily replace the straight conduit with a curved conduit and continue the operation without the need for an entirely new device.

In yet another preferred embodiment of this invention, the device has a safety mechanism that helps prevent the surgeon from inadvertently shooting the fastener into the patient until the proper moment. This mechanism works in conjunction with the triggering mechanism so that the means for propelling the fastener into the patient cannot be actuated until both the triggering means and the safety mechanism are actuated simultaneously.

Figure 4:
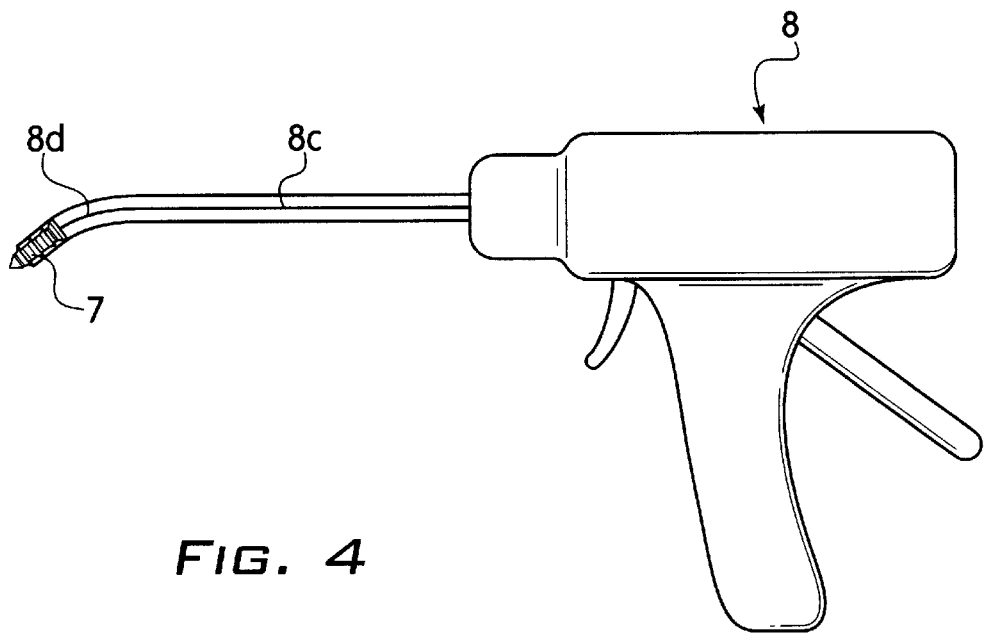
FIG. 4 is a schematic representation of a fastener according to the present invention being applied to a drillhole with a curved cannula in an area where no direct access could be achieved.

FIG. 4 describes an installation device (8) with a curved cannula (8c), inside of which is a fastener (1), which can be triggered from the cannula with a flexible piston (8d) into a tissue area where no direct access could be achieved.

Special attention must be directed to the relationship between the fastener and the cannula and piston of the installation instrument. The fastener must glide inside of the cannula easily but it should not be allowed to drop out of the cannula end by its own weight. The fastener should be capable of moving completely out of the cannula only when the piston pushes (strikes) it out into the drillhole in the plate and in the bodily tissue. Such behavior is attained, e.g., when the head of the fastener has a notch (as is described e.g. in FIG. 3 and in FIGS. 8B and C) into which the tip of the piston can be pushed. When the geometries of the notch and of the tip of the piston have been designed properly, a good frictional grip between the fastener and the piston can be achieved.

Another option is to make the dimensions of the fastener head and/or protuberances in relation to the inner diameters of the cannula such that a substantial friction exists between the fastener head and/or protuberances and the inner surface of the cannula, so that the fastener glides inside of the cannula only when it is pushed forward by means of the piston.

Figure 9:
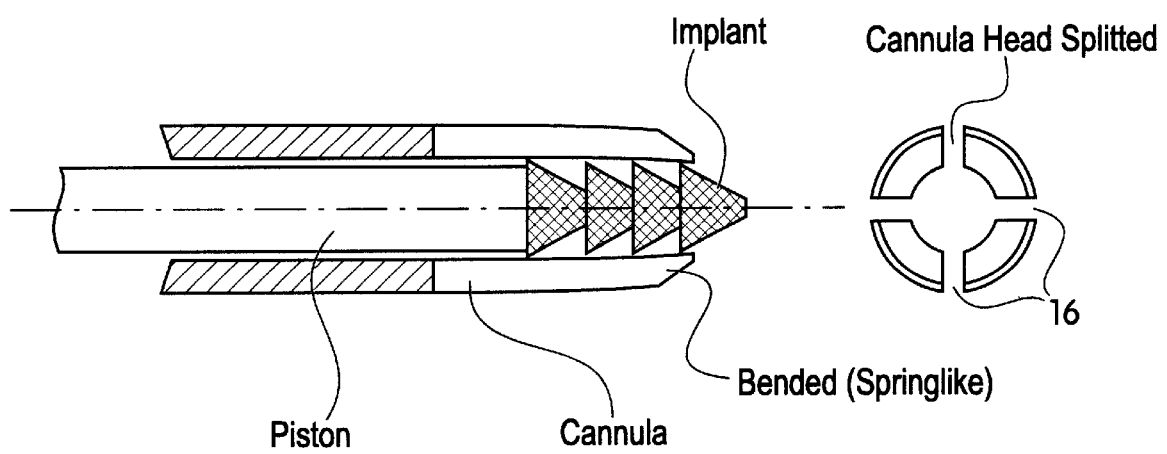
FIG. 9 shows schematically the tip of a cannula whose diameter has been decreased by splitting it and pressing the split parts to each other.

According to an advantageous embodiment of the invention, the diameter of the distal end of the instrument cannula is smaller than the diameter of its proximal end. In such a case, the fastener glides easily inside of the cannula, but cannot glide totally out of the cannula without a substantial push of the piston. FIG. 9 shows such an embodiment, where the distal part of the cannula has been split, e.g., by sawing to make grooves (16) which split the distal part of cannula into two or several (in this case, four) parts. These parts have been bent slightly so that the inner diameter of the distal part of the cannula is smaller than the diameter of the other parts of the cannula. The fastener can be pushed easily to the end (tip) of the cannula, but the reduced end of the cannula prevents the premature drop of the fastener out of cannula. The tip of the fastener, which can protrude out of the cannula, can be then located easily into the drillhole in the plate, until the strike of the piston pushes the fastener totally out of the cannula and into the drillhole.

The fixation fasteners and/or plates of the present invention can be manufactured by known techniques from known materials, such as thermoplastic bioabsorbable (resorbable or biodegradable) polymers, copolymers, polymer alloys, or composites, e.g., of poly-α-hydroxy acids and of other aliphatic bioabsorbable polyesters, polyanhydrides, polyorthoesters, polyorganophosphatzenes, tyrosine polymers and other bioabsorbable polymers disclosed in numerous publications, e.g., in S. Vainionpää et el., Prog. Polym. Sci., 14 (1989) 679-716, FI Pat. No. 952,884, FI Pat. No. 955,547 and WO-90/04982, EP 0449867 B1, U.S. Pat. No. 5,569,250, S.I. Ertel et al., J. Biomed. Mater. Res., 29 (1995) 1337-1348, the entire disclosures of which are incorporated herein by reference, as well as in the reference publications mentioned in the aforementioned publications.

Implants (plates and/or fasteners) in accordance with the invention can be manufactured of biodegradable polymers by using one polymer or a polymer alloy. The implants can also be reinforced by reinforcing the material by fibers manufactured of a bioabsorbable polymer or of a polymer alloy, or with biodegradable glassfibers, such as β-tricalsiumphosphate fibers, bioactive glassfibres or CaM fibers (as described in, e.g., EP146398, the entire disclosure of which is incorporated herein by reference). Ceramic powders can also be used as additives (fillers) in implants to promote new bone formation.

Implants according to the invention can also contain layered parts comprising, e.g., (a) a flexible outer layer as a surface layer improving the toughness and/or operating as a hydrolysis barrier and (b) a stiff inner layer. It is natural that the materials and implants of the invention can also contain various additives for facilitating the processability of the material (e.g. stabilizers, antioxidants or plasticizers) or for changing its properties (e.g. plasticizers or ceramic powder materials or biostable fibers, such as carbon) or for facilitating its treatment (e.g. colorants).

According to one advantageous embodiment, the implant of the invention contains some bioactive agent or agents, such as antibiotics, chemotherapeutic agents, agents activating healing of wounds, growth factor(s), bone morphogenic protein(s), anticoagulant (such as heparin) etc. Such bioactive implants are particularly advantageous in clinical use, because they have, in addition to their mechanical effect, also biochemical, medical and other effects to facilitate tissue healing and/or regeneration.

Because the plates contemplated by the present invention can be shaped (bent or twisted, etc.) in situ rapidly and at room temperature, either manually or with special bending tools (like forceps), the plates can be brought effectively into virtual conformance with the underlying bodily tissue being repaired, including damaged tissue having small radii of curvature, such as cranial and facial bones, even those of a small child. Thereafter, the plate can be fixed on bone rapidly and safely with fasteners of the invention, using the installation system of the invention. As a result, the bodily tissue on opposite sides of the severance or fracture is rapidly and effectively restrained against relative movement, whereby rapid, sturdy and non-disfiguring consolidation and/or healing of the bodily tissue is achieved.

Because, according to an advantageous embodiment, the plate shaping and fastener fixation procedures are done at room temperature, there is no risk of heat-related damage to biological tissue in the immediate vicinity of the treatment area, even in rather deep biological incisions, while such risk is a reality when using prior art plates which are shaped in situ by using heat.

Because the whole tissue fixation operation by using the system of the invention is done much more rapidly than when using prior art systems, surprising advantages are obtained: a shorter operation time results in smaller risks of operation complications and infections to the patient and considerable economic savings and/or increases of efficacy of operation room facilities.

The principles of the present invention described broadly above will now be described with reference to the following specific example, without intending to restrict the scope of the present invention.

EXAMPLE 1

A side of a fresh cadaver swine mandible was prepared by removing soft tissue from the testing surface of the bone. A bioresorbable bone fixation plate was then fixed to the bone with 4 bioabsorbable monocortical screws or fasteners of the invention.

Fixation plates, screws and fasteners were made from self-reinforced 70L/30DL PLA (Draw ration 3.5 to 5.5) (Manufacturer of Polymer is Boehringer Ingelheim Pharma KG, BU Fine Chemicals, PM Resomer, D-55216 Ingelheim, Germany, tel +49-(0)6132-77 2633, fax is +49(0)6132-77 4330, $M_w$=i.v. 5.5 to 7.0 dl/g). The plates were made with the method described in PCT/EP99/01438, the entire disclosure of which is incorporated herein by reference, and the screws and tacks were made according to PCT/FI 96/00511, the entire disclosure of which is incorporated herein by reference. The tack geometry was that of FIG. 1 of this invention. The Principal dimensions of the 6-hole fixation plate were 5.5 x 39 x 1.2 mm. The screws had a diameter of 2.0 mm and a length of 6 mm. The tack diameter was also 2.0 mm and length 6 mm.

Plate and screw fixation:

The fixation plate was laid on the bone. A screw hole of 1.5 mm diameter was drilled with an electric drilling machine into the bone through the screw hole of the plate. The drilled hole was then tapped with a tapping instrument of 2.0 mm diameter. The screw was driven through the screw hole of the plate and into the tapped screw hole with the manual screwdriver. The procedure was then repeated for 4 screws, leaving the innermost 2 screwholes of the 6-hole plate intact. That space was left free for a pullout testing jig.

Plate and tack fixation.

A fixation plate was laid on the bone as above. A hole of 2.0 mm diameter was drilled for the tack with the electric drilling machine into the bone through the screw hole of the plate. A tack was shot through the hole of the plate into the drillhole with the tack insertion instrument of the invention.

This procedure was repeated for 4 tacks, leaving the innermost 2 holes of the 6-hole plate intact. That space was left free for a pullout testing jig.

The total time used for each of the above fixations was measured with a stopwatch. The stopwatch was started before drilling the first drillhole and ended when all four screws or fasteners were inserted. Five parallel tests were performed for both fixation methods, and an assistant was serving instruments and implants to the operating surgeon.

Results

The total time used for inserting and fixing 4 screws in the above plate varied from 124 to 178 seconds, with an average of 156 seconds. The total time used for inserting and fixing 4 tacks in the above plate varied from 58 to 102 seconds, with an average of 76 seconds. This test showed that the time for fixation with the method of this invention took only about 50% of the time for fixation using the prior art method.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A surgical tissue fixation system comprising:
   (a) a bioabsorbable plate having an upper surface, a lower surface, and one or more holes extending through the plate from the upper surface to the lower surface, wherein said plate is deformable either at room temperature in operation room conditions or at an elevated temperature, and wherein said plate has sufficient strength and rigidity to fixate bone or other bodily tissue,
   (b) a bioabsorbable fastener adapted for rapid insertion by pushing into the plate's holes to secure the plate to underlying bodily tissue or bone and;
   (c) an installation instrument that is capable of installing the fasteners one after another, rapidly and securely and with a minimal trauma, into the holes extending through the plate and into the underlying bodily tissue or bone.

2. A surgical tissue fixation system according to claim 1, said fasteners further comprising a proximal head having a lower surface, and wherein said installation instrument is capable of installing the fasteners one after another precisely into the holes in the plate, so that the lower surface of the fastener's proximal head mates precisely with the upper surface of the plate.

3. A surgical tissue fixation system according to claim 2, wherein the fasteners further comprises a stem having protuberances and a distal conical tip, said stem being connected to the proximal head of said fastener.

4. A surgical tissue fixation system according to claim 3, wherein the protuberances on the stem of the fastener are elastically deformable so that they are capable of bending during installation of the fastener into the plate holes and further are capable of returning almost to their original position after installation of the fastener into the plate holes.

5. A surgical tissue fixation system according to claim 4, wherein said protuberances comprise ridges and at least part of said ridges contain logitudinal grooves.

6. A surgical tissue fixation system according to claim 4, wherein the fastener is cannulated.

7. A surgical tissue fixation system according to claim 6, said cannula having an inner diameter, an outer diameter, a proximal end and a distal end, wherein the distal end of the cannula is tapered such that the diameter of the distal end of the cannula is smaller than the inner diameter of the cannula.

8. A surgical tissue fixation system according to claim 1, said fasteners further comprising a proximal head having a lower surface and said one or more holes further comprising a countersink surface positioned at a point below the upper surface of the plate, and wherein said installation instrument is capable of installing the fasteners one after another precisely into the holes in the plate, so that the lower surface of the fastener's proximal head mates precisely with the countersink surface of the hole.

9. The tissue fixation system of claim 1, wherein the installation instrument that is capable of installing the fasteners by shooting them into the holes extending through the plate and into the underlying bodily tissue or bone.

10. A surgical tissue fixation system comprising:
    a bioabsorbable plate including one or more holes, wherein the plate is deformable either at room temperature in operation room conditions or at an elevated temperature, and wherein said plate has sufficient strength and rigidity to fixate bone or other bodily tissue;
    a bioabsorbable fastener including a stem from which elastically deformable protruberances extend, wherein the elastically deformable protruberances are capable of bending temporarily during installation of said fastener by pushing into said plate and further said protruberances are capable of almost returning to their original state following installation of said fastener, and wherein said fastener secures the plate to underlying bodily tissue or bone and;
    an installation instrument that is capable of installing the fasteners one after another, rapidly and securely and with minimal trauma extending through the holes in the plate into the underlying bodily tissue or bone.

11. A surgical tissue fixation system comprising:
    a bioabsorbable plate including one or more holes, wherein the plate is deformable either at room temperature in operation room conditions or at an elevated temperature, and wherein said plate has sufficient strength and rigidity to fixate bone or other bodily tissue;
    a bioabsorbable fastener for insertion into the plate's holes by pushing to secure the plate to the underlying bodily tissue or bone and;
    an installation instrument including a cannula, wherein a distal end of the cannula is smaller than the diameter of a proximal end of the cannula, and further wherein said installation instrument is capable of installing into the plate's holes.

12. A surgical tissue fixation system comprising:
    (a) a bioabsorbable plate having an upper surface, a lower surface, and one or more holes extending through the plate from the upper surface to the lower surface, wherein said plate is deformable either at room temperature in operation roon conditions or at an elevated temperature, and wherein said plate has sufficient strength and rigidity to fixate bone or other bodily tissue;
    (b) a bioabsorbable fastener adapted for rapid insertion into the plate's holes to secure the plate to underlying bodily tissue or bone, wherein said fasteners include a proximal head having a lower surface and;
    (c) an installation instrument including a curved cannula that is capable of installing the fasteners one after another, rapidly, securely, precisely, and with minimal trauma, into the holes extending through the plate and into the underlying bodily tissue or bone so that the lower surface of the fastener's proximal head mates precisely with the upper surface of the plate.

13. The surgical tissue fixation system of claim 12, said curved cannula having an inner diameter, an outer diameter, a proximal end, and a distal end, wherein the distal end of the cannula is tapered such that the diameter of the distal end of the cannula is smaller than the inner diameter of the cannula.

* * * * *